United States Patent
Dang et al.

(10) Patent No.: US 11,583,498 B2
(45) Date of Patent: Feb. 21, 2023

(54) PROCESS FOR PRODUCING A TAN IIA NANOLIPOSOME SYSTEM FOR FOODS AND MEDICAL PRODUCTS

(71) Applicant: Wakamono Corporation, Ho Chi Minh (VN)

(72) Inventors: Hong Ngoc Thi Dang, Ho Chi Minh (VN); Nam Hai Lai, Ho Chi Minh (VN)

(73) Assignee: WAKAMONO CORPORATION, Ho Chi Minh (VN)

( * ) Notice: Subject to any disclaimer, the term of this patent is extended or adjusted under 35 U.S.C. 154(b) by 49 days.

(21) Appl. No.: 17/127,144

(22) Filed: Dec. 18, 2020

(65) Prior Publication Data

US 2021/0205220 A1 Jul. 8, 2021

(30) Foreign Application Priority Data

Jan. 3, 2020 (VN) .............................. 1-2020-00059

(51) Int. Cl.
*A23L 33/105* (2016.01)
*B82Y 5/00* (2011.01)
(Continued)

(52) U.S. Cl.
CPC .......... *A61K 9/1277* (2013.01); *A23L 33/105* (2016.08); *A61K 36/537* (2013.01); *B82Y 5/00* (2013.01)

(58) Field of Classification Search
None
See application file for complete search history.

(56) References Cited

U.S. PATENT DOCUMENTS

2013/0089600 A1* 4/2013 Winnicki ............... A61K 47/24
514/454
2017/0080000 A1* 3/2017 Hodgson ................... A61P 3/00

FOREIGN PATENT DOCUMENTS

CN 1839819 A * 10/2006

OTHER PUBLICATIONS

Colloid Metrix. "Inline particle size measurement of micelles." accessed at https://www.colloid-metrix.de/fileadmin/pdf_applications/CMX_Liposomes_Micelles_EN.pdf on May 2, 2022, pp. 1-5. (Year: 2022).*

(Continued)

*Primary Examiner* — Isaac Shomer
(74) *Attorney, Agent, or Firm* — Fulwider Patton LLP

(57) ABSTRACT

The invention relates to a process for producing a Tan IIA nanoliposome system for foods and medical products, comprises: (i) preparing a dispersed phase by dissolving Tan IIA in ethanol in a Tan IIA weight:ethanol volume ratio of 8:10 by a stirrer at 300-500 rpm with heating to 40-60° C. within 4-8 hours; (ii) preparing a liposome carrier consisting of lecithin and olive oil in a ratio of 1:3 by weight by mixing in a constant temperature bath at 40-60° C. to ensure that lecithin is completely dissolved in the oil while stirring; (iii) adding the carrier to the dispersed phase in a ratio of 40:60 by weight, further heating the carrier and dispersed phase mixture to 40-60° C. and stirring at 800-1000 rpm within 1 to 2 hours; (iv) cooling the resulting mixture to 25° C. and pumping the cooled mixture, using an ultrasonic atomizer nozzle at 60 Hz (10-20 μm droplet size, 10 mL/min), into 1-1.5 L of distilled water (with the temperature of the distilled water at 25° C.) to obtain a liposome suspension-water mixture; (v) homogenizing the liposome suspension-water mixture by pumping through a high pressure homogenizer at 30 Mpa to obtain a Tan IIA nanoliposome system (Continued)

as a homogeneous and stable mixture with a confirmed particle size smaller than 200 nm.

1 Claim, 1 Drawing Sheet

(51) Int. Cl.
*A61K 9/127* (2006.01)
*A61K 36/537* (2006.01)

(56) References Cited

OTHER PUBLICATIONS

JN Israelachvili, S Marcelja, and RG Horn. "Physical principles of membrane organization." Quarterly Reviews of Biophysics, vol. 13(2), 1980, pp. 121-200. (Year: 1980).*
Google Translate. English Translation of CN 1839819 A. https://patents.google.com/patent/CN1839819A/en?oq=CN+1839819 accessed May 3, 2022, originally published in Chinese on Oct. 4, 2006, pp. 1-16. (Year: 2006).*
Paola Sánchez-Moreno et al. "Characterization of Different Functionalized Lipidic Nanocapsules as Potential Drug Carriers." International Journal of Molecular Sciences, vol. 13, 2012, ISSN 1422-0067, pp. 2405-2424. (Year: 2012).*
Nakonechny et al. Olive Oil-Based Delivery of Photosensitizers for Bacterial Eradication, Olive Oil - Constituents, Quality, Health Properties and Bioconversions, Dr. Dimitrios Boskou (Ed.), ISBN: 978-953-307-921-9, 2012, Chapter 26, pp. 471-492 and one additional page. (Year: 2012).*

* cited by examiner

PROCESS FOR PRODUCING A TAN IIA NANOLIPOSOME SYSTEM FOR FOODS AND MEDICAL PRODUCTS

CROSS-REFERENCES TO RELATED APPLICATIONS

This application claims priority to Vietnam Application No. 1-2020-00059, filed Jan. 3, 2020, the content of which is incorporated herein by reference in its entirety.

BACKGROUND OF THE INVENTION

The invention relates to a process for producing a Tan IIA nanoliposome system for foods and medical products.

Tan IIA, or Tanshinone IIA, is extracted from the roots of danshen or *Salvia miltiorrhiza* Bunge in the Labiatae family. Danshen has been widely used in Oriental countries, particularly China, to treat different circulatory disorders due to its different pharmacological effects, including vasodilation, anticoagulation, anti-inflammation, and reduction of free radicals. Tan IIA helps adjust or prevent the metastases of cancer cells by adjusting the adhesion molecules. In addition, other studies have proved that Tan IIA is capable of strong anti-inflammation and anti-oxidation. However, Tan IIA has low bioavailability, which via oral administration, according to a study by Lu Xing et al in 2017, has been proved to affect the clinical applicability of the compound.

Therefore, it is necessary to improve the absorbability and increase the bioavailability of the compound. The application of nanotechnology is a new technological application to produce a drug delivery system and increase the bioavailability of a compound. Particularly, the liposome system according to the invention is a new system with a structure of spherical micromolecules of very small (nano) size, the core of which containing active nutrients and being encapsulated by one or more phospholipid bilayers, which is capable of accurately containing, protecting, delivering, and releasing correctly dosed active compounds to desired sites within the body. Tan IIA is packed in the nano drug delivery system to help selectively, effectively, and economically deliver the compound to the targets. In Vietnam, nanotechnology is still new in biomedicine, and does not yet have many applications, but has attracted a lot of research interests. Currently, the most popular studies are about the application of nano curcumin and the drug delivery systems to targeted cells, and there has not been any study on the production of nano Tan IIA. The use of a nanoparticle-forming liposome system to carry drug and release drug is a new direction to treat diseases and an application to other products. Patent Publication No. CN104352438A "Tanshinone II A liposome combination drug, as well as large-scale industrial production process and application thereof" relates to a process for producing liposome particles with a size of 150-1000 nm, which is a process for producing a Tan IIA liposome system used in medicinal products. However, the process for producing liposome particles further produces nonuniform large-sized particles, which makes it difficult for production.

Patent Publication No. CN102697664A "Tanshinone lipidosome and preparation method thereof" relates to a process for producing particles smaller than 200 nm, which is an applied process in cosmetics using surfactants, not applicable to foods and medical products.

Known processes for producing nano Tan IIA produce nonuniform large-sized microparticles, particularly, nano Tan IIA according to a liposome formula of liposome particles with a size larger than 200 nm, so the effects of solubility in water and effects of use are not great.

Therefore, there is a need for a process for producing a Tan IIA nanoliposome system for foods and medical products comprising uniform liposome microparticles with a size smaller than 200 nm with preferable water solubility, while still retaining its structure and Tan IIA activity during nanoization.

SUMMARY OF THE INVENTION

The object of the invention is to provide a process for producing a Tan IIA nanoliposome system for foods and medical products in order to overcome the disadvantages of known processes to produce uniform particles with a size smaller than 200 nm which are capable of dissolving in water, wherein the unchanged activity and structure thereof help increase the effects of use of the active Tan IIA, particularly increasing the absorbability and bioavailability.

To achieve the above object, the process for producing a Tan IIA nanoliposome system for foods and medical products according to the present invention comprises:

(i) Step 1: preparing a dispersed phase by dissolving Tan IIA in ethanol in a Tan IIA weight:ethanol volume ratio of 8:10 by a stirrer at 300-500 rpm, while heating to 40-60° C. within 4-8 hours;

(ii) Step 2: preparing a liposome carrier consisting of lecithin and olive oil in a ratio of 1:3 by weight mixed in a constant temperature bath at 40-60° C. to ensure that lecithin is completely dissolved in the oil under evenly stirring.

(iii) Step 3: adding the liposome carrier to the dispersed phase in a ratio of 40:60 by weight, further heating the carrier and dispersed phase mixture to 40-60° C. and stirring at 800-1000 rpm for 1-2 hours.

(iv) Step 4: cooling the resulting mixture to 25° C. and pumping the cooled mixture, using an ultrasonic atomizer nozzle at 60 Hz (10-20 μm droplet size, 10 mL/min), into 1-1.5 L of distilled water with the temperature of the distilled water at 25° C., to obtain liposome suspension-water;

(v) Step 5: homogenizing the liposome suspension-water mixture by pumping through a high pressure homogenizer at 30 Mpa to obtain a Tan IIA nanoliposome system.

DETAILED DESCRIPTION OF THE INVENTION

Figure 1:
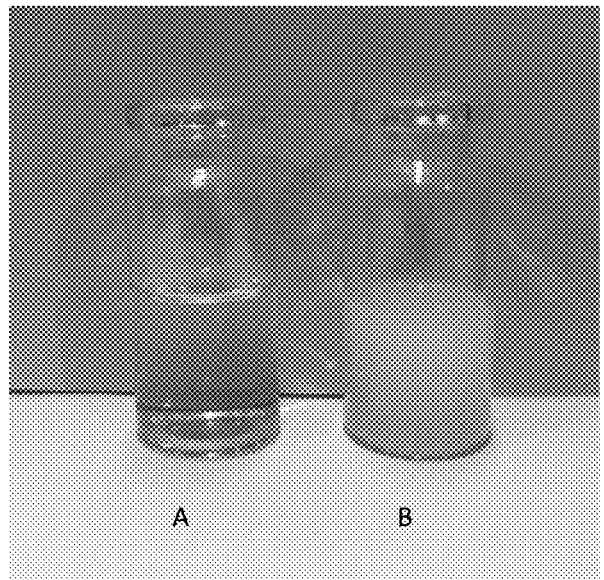
FIG. 1 is a comparative drawing of the water dispersibility between the known Tan IIA and nano Tan IIA obtained by a process for producing a Tan IIA nanoliposome system for foods and medical products according to the present invention.

A process for producing a Tan IIA nanoliposome system for foods and medical products according to the present invention is conducted as follows:

(i) Step 1: Prepare a dispersed phase by dissolving Tan IIA in ethanol in a Tan IIA weight:ethanol volume ratio of 8:10 by a stirrer at 300-500 rpm, while heating to 40-60° C. for 4-8 hours. Ethanol is used as a solvent since it is capable of dissolving Tan IIA well, which produces a preferable dispersed phase and allows the dispersed phase to combine with a preferable PEG carrier. The use of ethanol having a hydroxyl (OH—) residue bonded with water has an effect of stabilizing the structure of the oil-in-water liposome system. Via experiments, it is able to determine the Tan IIA:ethanol ratio as 8:10 (weight:volume), and obtain Tan IIA with the highest solubility and avoid excess ethanol waste. The use of stirring and heating to produce Tan IIA with preferable dispersibility, in experiments of different stirring and temperature conditions, shows that at 300-500 rpm and with heating to 40-60° C., the Tan IIA dispersed phase is better and is combined with a preferable PEG carrier.

(ii) Step 2: Prepare a liposome carrier consisting of lecithin and olive oil in a ratio of 1:3 by weight by mixing in a constant temperature bath at 40-60° C. to ensure that lecithin is completely dissolved in the oil under evenly stirring.

When used, Tan IIA is usually destroyed in the gastrointestinal tract, and partially absorbed into the blood, while the rest is cleared therefrom. Therefore, there is a need for a process for producing microparticles containing small-sized active Tan IIA with biofilm, stable structure, no aggregation, and high solubility. Since the Tan IIA nanoliposome system according to the present invention has been used in cosmetic and pharmaceutical industries, the compounds selected for use have to be highly safe, and have no toxicity and few side effects.

Surfactants are used to stabilize and homogenize the system, and prevent flocculation and aggregation of the system compounds, wherein lecithin (phospholipid) is used herein. In this process, lecithin from soybean, which is safe for human use and has a reasonable price, is used. The molecular formula of lecithin according to the publication of Willstatter in 1918 consists of glycerophosphoric acid, fatty acid, and choline, wherein the three components can be combined in various ways to make various types of lecithin. Two fatty acid molecules are attracted to each other so they arrange in the same direction, with the heads of the fatty acids having hydrophobic residues that form the hydrophobic portion of lecithin. The $C_2$-$C_3$ bond in glycerin residue can be rotated at an angle of 180° to cause the polar P group to be in the reverse direction of the fatty acid chain, forming the hydrophilic portion of lecithin. For this special structure, lecithin is both hydrophilic and hydrophobic (lipophilic). This is an advantage of using lecithin to produce a liposome system. The liposome system may lock water soluble (hydrophilic) active solutes in the vesicles containing water inside and water insoluble (hydrophobic) active solutes in bilayers thereof. The latter allows for the use of liposome to form Tan IIA nanoparticles that are compatible with water. After many experiments, lecithin and olive oil are used in a ratio of 1:3 by weight to produce the most stable system.

(iii) Step 3: Add the carrier to the dispersed phase in a ratio of 40:60 by weight, further heating the carrier and dispersed phase mixture to 40-60° C. and stirring at 800-1000 rpm for 1-2 hours.

(iv) Step 4: Cool the resulting mixture to 25° C. and pump, using an ultrasonic atomizer nozzle at 60 Hz (10-20 μm droplet size, 10 mL/min), into 1-1.5 L of distilled water (with the temperature of the distilled water at 25° C.). Concentrate the liposome suspension-water by rotary evaporation at 20-30 mmHg and below 55° C.

The nanoparticles that are likely to aggregate require enough energy to break the bonding for dispersion thereof. The use of the ultrasonic atomizer nozzle, as an effective means of dispersing the nanoparticles and reducing the nanoparticle size, produces more uniform particles with a smaller size. The dispersion and aggregate disruption of the nanoparticles results from gas permeation by ultrasonic waves. When the ultrasound spreads into the solvent, it will continuously create alternating cycles between the high pressures and low pressures, which makes an impact on the bonding of the nanoparticles. Simultaneously, when series of bubbles burst, they will make a great pressure on the nanoparticle clusters to separate them easily.

(v) Step 5: Homogenize the liposome suspension-water mixture by pumping through a high pressure homogenizer at 30 Mpa (300 bar). Homogenize the liposome suspension-water mixture to reduce the size of the dispersed phase particles and evenly distribute them in the continuous phase to limit the phase separation by gravity, ensuring of uniformity, solution stability, and extension on the expiration date of the product.

The use of ultrasonication helps make an impact on the nanoparticles, making it difficult to aggregate them together. However, this method has a disadvantage that the ultrasonic end is made of metal, so during high intensity ultrasonication, it may expose the product to titanium. To ensure that it is safe for the product, it has been experimented and the 60 hz frequency is selected to separate the nanoparticles while maintaining the product safety. However, at this frequency, the nano product cannot maintain the particle stability for long, and the expiration date of the product is short. To extend the expiration date and the particle stability, perform pumping the solution obtained from step 4 via a high pressure homogenizer at 30 Mpa to ensure of uniformity, solution stability, and extension on the expiration date of the product.

The liposome system obtained by the process according to the present invention has a pH of 7-7.5. With this pH value, the microparticles are stable since in such neutral medium, the bond between Tan IIA and the carrier is retained during dispersion, while when the nano liposome system has pH<7, the bond weakens, which leads to the destruction of Tan IIA nanoparticles in the gastrointestinal tract.

The Tan IIA nanoliposome system obtained by the process according to the present invention, which has a hydrophilic lipophilic balance (HLB—an amphiphilic balance ranging from 0 to 40) of 13-18, is a hydrophilic liposome system. This liposome system comprises hydrophilic and non-aggregated microparticles containing Tan IIA, wherein the stable particle size is 10-200 nm, so it may easily permeate through the cell membrane for full effects and increase the solubility of Tan IIA in water, thereby increasing the bioavailability of the compound.

EXAMPLES

Example: Production of 1000 g of Tan IIA Nanoliposome System

A dispersed phase was prepared by dissolving 80 g of Tan IIA in 100 mL of ethanol by C-MAG HS4/7/10 magnetic stirrer with heating from KIA—Germany at 400 rpm, while heating to 50° C. in 6 hours. 180 g of the dispersed phase was obtained.

A liposome carrier consisting of 30 g lecithin and 90 g olive oil was prepared by mixing in Labtech LWB-106D constant temperature bath (1200 W, 50° C.) to ensure that lecithin was completely dissolved in olive oil. Stirring was continued in 30 min to obtain 120 g of the carrier solution.

120 g the carrier was added to 180 g of the dispersed phase while heating the carrier and dispersed phase mixture to 50° C. and stirring at 900 rpm in 2 hours by C-MAG HS 4/7/10 magnetic stirrer with heating from KIA—Germany.

The resulting mixture was cooled to 25° C. and pumped, by using an ultrasonic atomizer nozzle, 100W, 30 Khz) at 60 Hz (10-20 μm droplet size, 10 mL/min) into 1 L of distilled water (25° C.), giving a liposome suspension-water mixture. The liposome suspension-water was concentrated by rotary evaporation at 25 mmHg and below 55° C. until there was 1000 g of the suspension mixture left.

The liposome suspension-water mixture was homogenized by pumping through a high pressure homogenizer at 30 Mpa. 1000 g of the Tan IIA nanoliposome system obtained was a homogeneous and stable mixture, with a confirmed particle size smaller than 200 nm.

By UV-vis spectroscopy, the inventors observed that the peak positions of the Tan IIA material and the Tan IIA nanoliposome system completely matched. This showed that the liposome system obtained by the process according to the present invention still retained its structure and Tan IIA activity during nanoization. UV-Vis spectroscopy was used to quantify the content of Tan IIA in the liposome system. The results showed that Tan IIA concentration in the Tan IIA nanoliposome system was 8-10%.

Figure 2:
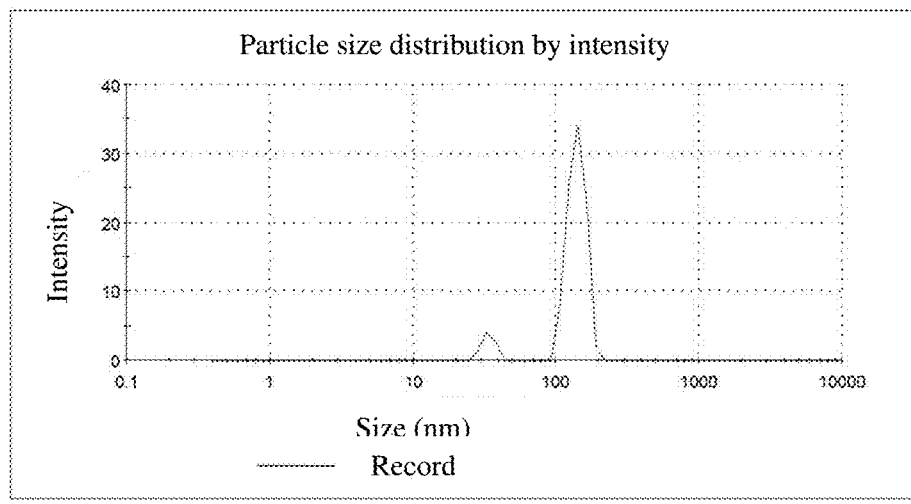
FIG. 2 is a TEM spectrum of the size of liposome nanoparticles Tan IIA obtained by a process for producing a Tan IIA nanoliposome system for foods and medical products according to the present invention.

The size of Tan IIA nanoparticles, which was measured by transmission electron microscopy (TEM) as shown in FIG. 2, showed that the particle size was 10-200 nm accounting for 81.3% of the solution.

Particle size measured by DLS: The particles suspended in a liquid kept being subjected to random movements, and the particle size directly affected the particle rate. Small particles moved faster than larger particles. In DLS, the light through the sample and the scattering light were detected and recorded at a certain angle.

Zeta potential or dynamic potential: the potential between the dispersed phase and the dispersion medium.

| Size (nm, from TEM) | Size (nm, from DLS) | Zeta potential (mV) | Stability (month) | Water solubility |
|---|---|---|---|---|
| 10-200 | 10-200 | −40 | >12 | Good solubility in water, system stability >30 days after the dissolution in water |

From the above results, it was shown that the liposome system of microparticles with a size smaller than 200 nm, have great stability (>12 months), good water solubility, and system stability of more than 30 days after the dissolution in water.

With reference to FIG. 1, water dispersibility was compared between the known 95% Tan IIA and nano Tan IIA obtained by the process according to the present invention, in which Vial A represented the known 95% Tan IIA dispersed in water, Vial B represented nano Tan IIA dispersed in water obtained by the process according to the present invention. FIG. 1 showed the known water insoluble 95% Tan IIA, wherein the particles suspended in water, and the solution was slurry and sedimented at the bottom of the vial over a period of time (B); nano Tan IIA obtained by the process according to the present invention completely dissolved in water to form a transparent and homogeneous solution (A).

FIG. 2, a TEM spectrum of the size of Tan IIA nanoparticles obtained by the process according to the present invention, showed that the average particle size was 10-200 nm.

The process for producing a Tan IIA nanoliposome system for foods and medical products according to the present invention has succeeded in producing a liposome system, comprising uniform Tan IIA nanoparticles with a size smaller than 200 nm and with good solubility in water, while still retaining its structure, and Tan IIA activity during nanoization.

The compounds used in the process for producing nano Tan IIA dispersed well in water and was highly safe, nontoxic, and had few side effects, so the Tan IIA nanoliposome system obtained from the process according to the present invention was highly safe when used.

The process according to the present invention was simple, easy to perform, and appropriate under the practical conditions in Vietnam.

We claim:

1. A process for producing a Tanshinone IIA nanoparticle composition for foods and medical products, comprising:
   (i) preparing a dispersed phase by dissolving Tanshinone IIA in ethanol in a Tanshinone IIA weight:ethanol volume ratio of 8:10 by a stirrer at 300-500 rpm, while heating to 40-60° C. within 4-8 hours;
   (ii) preparing a carrier consisting of lecithin and olive oil in a ratio of 1:3 by weight by mixing in a constant temperature bath at 40-60° C. to ensure that lecithin is completely dissolved in the oil while evenly stirring;
   (iii) adding the carrier to the dispersed phase in a ratio of 40:60 by weight, further heating the carrier and dispersed phase mixture to 40-60° C. and stirring at 800-1000 rpm for 1-2 hours;
   (iv) cooling the resulting mixture to 25° C. and pumping the cooled mixture, using an ultrasonic atomizer nozzle at 60 Hz having a 10-20 μm droplet size; at a rate of 10 mL/min, into distilled water with a temperature of the distilled water at 25° C., to obtain a suspension-water mixture; and
   (v) homogenizing the suspension-water mixture by pumping through a high pressure homogenizer at 30 Mpa to obtain a Tanshione IIA nanoparticle composition.

* * * * *